(12) United States Patent
Kang et al.

(10) Patent No.: US 9,034,614 B2
(45) Date of Patent: May 19, 2015

(54) METHOD OF PREPARING ALKYL BUTYRATE FROM FERMENTED LIQUID USING MICROORGANISMS

(75) Inventors: Sin Young Kang, Daejeon (KR); Min Su Koo, Daejeon (KR); In Ho Cho, Seoul (KR); Joon Sik Lee, Daejeon (KR); Eun Hee Park, Daejoen (KR); Joong Min Park, Daejeon (KR); Jae Yeon Park, Seoul (KR); Young Hwan Chu, Daejeon (KR); Dong Hyun Kim, Seoul (KR); Woo Chan Park, Jeollabuk-do (KR); Seung Yeop Lee, Daejeon (KR); Jae Wook Ryu, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 147 days.

(21) Appl. No.: 13/821,109

(22) PCT Filed: Sep. 8, 2011

(86) PCT No.: PCT/KR2011/006647
§ 371 (c)(1),
(2), (4) Date: Mar. 6, 2013

(87) PCT Pub. No.: WO2012/033359
PCT Pub. Date: Mar. 15, 2012

(65) Prior Publication Data
US 2013/0164801 A1 Jun. 27, 2013

(30) Foreign Application Priority Data

Sep. 8, 2010 (KR) .................. 10-2010-0087990
Sep. 7, 2011 (KR) .................. 10-2011-0090570

(51) Int. Cl.
*C12P 7/62* (2006.01)
*C07C 51/02* (2006.01)
(Continued)

(52) U.S. Cl.
CPC . *C12P 7/62* (2013.01); *C07C 51/02* (2013.01); *C07C 51/48* (2013.01); *C12P 7/52* (2013.01)

(58) Field of Classification Search
CPC ............. C12P 7/62; C12P 7/52; C07C 51/02; C07C 51/48
See application file for complete search history.

(56) References Cited

U.S. PATENT DOCUMENTS

2009/0127092 A1 5/2009 Tedder
2011/0294176 A1 12/2011 Kang et al.
2011/0300596 A1 12/2011 Lee et al.

FOREIGN PATENT DOCUMENTS

WO 2009120042 A2 10/2009
WO 2010068052 A2 6/2010
WO 2010074469 A2 7/2010

OTHER PUBLICATIONS

Kang et al., machine translation of WO 2010/074469; published Jul. 1, 2010.*

(Continued)

*Primary Examiner* — Karen Cochrane Carlson
*Assistant Examiner* — Jennifer M. H. Tichy
(74) *Attorney, Agent, or Firm* — Abelman, Frayne & Schwab (57) ABSTRACT

Disclosed is a method of preparing alkyl butyrate, which comprises: (a) producing a fermented liquid containing butyrate salt through a fermentation process using butyric acid-producing strains; (b) obtaining an extracted liquid containing butyric acid from a continuous extracting apparatus using an extraction solvent, after converting the butyrate salt into butyric acid by adding an inorganic acid except for carbonic acid or carbon dioxide into the fermented liquid, wherein the continuous extracting apparatus includes a plurality of extraction plates which are installed inside an extraction column and perform a reciprocating motion vertically, and the broth and the extraction solvent are supplied to upper and lower portions of the column, respectively; and (c) reacting the extracted liquid and alcohol having a carbon number of 4 or less or a mixture thereof in an esterification reactor to convert a resultant product into alkyl butyrate. According to the present invention, butyric acid existing in microbic culture fluid can be efficiently extracted, and furthermore, competitively priced alkyl butyrate can be prepared without an additional process of separating the extracted solvent while minimizing energy consumption.

6 Claims, 4 Drawing Sheets

(51) Int. Cl.
*C07C 51/48* (2006.01)
*C12P 7/52* (2006.01)

(56) References Cited

OTHER PUBLICATIONS

Zetang Wu, et al., "Extractive Fermentation for Butyric Acid Production From Glucose by *Clostridium tyrobutyrictim*," Biotechnology and Bioengineering, vol. 82, No. 1, pp. 93-102 (Apr. 5, 2003).
International Search Report for PCT/KR2011/006647 dated Apr. 5, 2012 (English translation) (2 pages).
International Preliminary Report on Patentability for PCT/KR2011/006647 dated Mar. 13, 2013 (7 pages).
Roffler et al.; "In Situ Extractive Fermentation of Acetone and Butanol"; Biotechnology and Bioengineering, vol. 31; pp. 135-143; 1988.
Office Action dated Feb. 28, 2014 issued by the Chinese Patent Office.
Supplementary European Search report dated Oct. 1, 2014 for PCT/KR2011006647 (2 pages).

\* cited by examiner

METHOD OF PREPARING ALKYL BUTYRATE FROM FERMENTED LIQUID USING MICROORGANISMS

RELATED APPLICATIONS

This application is a United States national phase application under 35 USC §371of PCT/KR2011/006647 filed on Sep. 8, 2011, and claims the benefit under 35 USC §119 of Korean patent application numbers KR 10-2010-0087990 filed Sep. 8, 2010 and KR 10-2011-0090570 filed Sep. 7, 2011, the disclosures of which are incorporated herein by reference in their entireties.

TECHNICAL FIELD

The present invention relates to a method of preparing alkyl butyrate from fermented liquid using microorganisms, and, more particularly, to a method of preparing alkyl butyrate which may be used as fuel oil by extracting butyric acid produced using a butyric acid production strain, with a solvent.

BACKGROUND ART

Recently, many studies regarding technological developments and projects related to bio-ethanol fuel have been published. However, the biggest problem with using bio-ethanol as a blending agent of fuel oil is that, upon introduction of water to ethanol-mixed gasoline, a water-ethanol mixture layer is separated from gasoline while water is absorbed into the mixed gasoline.

Gasoline mixed with butanol, methyl ester or ethyl butyrate, unlike such ethanol, does not absorb water even when water is introduced thereto, and thus layer separation thereof does not occur. Thus, gasoline mixed with butanol, methyl butyrate or ethyl butyrate does not need additional treatment in storage, transport infrastructure and vehicles, unlike ethanol-mixed gasoline.

The additional advantages of butanol, methyl butyrate and ethyl butyrate are that a heat value is higher and vapor pressure is lower than ethanol, thus decreasing a probability of generating vapor lock in engines for vehicles. In particular, because butanol has an air-to-fuel ratio close to that of gasoline, compared to ethanol, it may be added in a comparatively larger amount to gasoline in the range that does not affect performance of engines.

As shown in Table 1 below, however, butanol has an octane number approximately equal to that of gasoline, making it difficult to use as an octane booster such as ethanol, MTBE, or ETBE.

Methyl butyrate and ethyl butyrate are superior octane boosters to MTBE, and are not harmful to the human body to the extent of being useful as a fruity flavor, and are thus regarded as a material harmless to the environment and the human body when added to gasoline.

TABLE 1

|  | Gasoline | Ethanol | Butanol | Methyl butyrate | Ethyl butyrate |
|---|---|---|---|---|---|
| Solubility in water | Insoluble | Miscible | 9.1 cc/100 cc | 15 g/L | 4.9 g/L |
| Molecular weight & molecular formula | — | 46 | 74 | 102 | 116 |
|  | $C_4$-$C_{12}$ | $C_2H_5OH$ | $C_4H_5OH$ | $C_5H_{10}O_2$ | $C_5H_{12}O_2$ |
| Density @20° C., g/cm$^2$ | 0.72 | 0.79 | 0.81 | 0.898 | 0.879 |
| Boiling point, ° C. | 32-210 | 78 | 117 | 102 | 121 |
| Flash point, ° C. | −20 | 12 | 35 | 12 | 26 |
| Heat value, Kcal/kg | 7,700 | 5,076 | 6,404 | 6,094 | 6,443 |
| Evaporation heat, Kcal/kg | 86 | 200 | 142 | — | — |
| Air/fuel ratio | 14.6 | 9.0 | 11.2 | — | — |
| Blending octane number (RON) | 91~99 | 129 | 96 | 125 | 123 |
| Vapor pressure @ 100 F., kPa | — | 14.9 (106-168) | 1.23 (23-30) | 24.4 | 1.5 |

Despite the above advantages, the main reason why butyric acid derivatives such as methyl butyrate and ethyl butyrate are not used as fuel is that efficient production of butyric acid has not yet been achieved.

As mentioned above, methyl butyrate and ethyl butyrate may be used as octane boosters for gasoline blending, and ethyl butyrate may also be utilized as a solvent.

Moreover, as shown in Table 2 below, butyl butyrate has a cetane number of about 30, and a flash point which satisfies the standard of diesel, and thus may be utilized as novel bio-diesel. When butyl butyrate is hydrogenolyzed, only butanol is produced without generation of other ester byproducts, and thus, among ester compounds, butyl butyrate may be optimal for producing butanol.

TABLE 2

|  | Diesel | Ethyl butyrate | Butyl butyrate | Soybean bio-diesel |
|---|---|---|---|---|
| Solubility in water | Insoluble | 4.9 g/L | Insoluble | Insoluble |
| Molecular weight & molecular formula | — | 116 | 144 | RCOOCH$_3$ |
|  |  | $C_5H_{12}O_2$ | $C_3H_7COOC_4H_5$ |  |
| Density @20° C., g/cm$^2$ | 0.82 | 0.879 | 0.8692 | 0.87-0.89 |
| Boiling point, ° C. | 150~380 | 121 | 165 | 340-380 |
| Flash point, ° C. | 40 or more | 26 | 49 | 180-185 |

TABLE 2-continued

|  | Diesel | Ethyl butyrate | Butyl butyrate | Soybean bio-diesel |
|---|---|---|---|---|
| Heat value, Kcal/kg | 9,100 | 6443 | 6,350 | 8,300 |
| Blending cetane number | 50 | 0-13 | 25-30 | 40-45 |

In the case of a butyrate present in the form of a salt in a fermented liquid, that is, a broth, resulting from microorganism strains, even when alkylamine, which is a basic organic solvent having good extraction efficiency, is used as an extraction solvent, it is very difficult to extract butyric acid.

Conventional methods are disclosed in such a manner that an inorganic acid such as sulfuric acid is added to a broth so that a butyrate salt is converted into butyric acid, after which butyric acid is extracted with an extraction solvent. However, as a spent broth obtained after extraction contains ammonium sulfate or calcium sulfate, it is impossible to recover ammonia and calcium hydroxide from the broth, undesirably increasing the production cost.

On the other hand, butyric acid is esterified with the addition of butanol, and then hydrogenolyzed using a catalytic reactor, thus preparing butanol, which is disclosed in Korean Unexamined Patent Application Publication No. 2009-0103720.

However, processes of preparing low-molecular-weight alkyl ester useful as fuel oil from bio-derived butyric acid, in particular, microorganism-derived butyric acid, have not yet been known.

DISCLOSURE

Technical Problem

Accordingly, the present invention has been made keeping in mind the above problems occurring in the related art, and the present invention is intended to provide a process of preparing alkyl butyrate without the use of an expensive high-pressure high-temperature catalytic reactor, while efficiently extracting butyric acid from a broth using microorganisms.

An aspect of the present invention is to provide a method of preparing alkyl butyrate, which includes (a) producing a broth including a butyrate salt via fermentation using a butyric acid production strain; (b) adding an inorganic acid other than carbonic acid, or carbon dioxide to the broth so that the butyrate salt is converted into butyric acid, and then extracting butyric acid using an extraction solvent by means of a continuous extraction apparatus, thus obtaining an extract containing butyric acid, wherein the continuous extraction apparatus is configured such that an extraction column is provided with a plurality of plates which perform a reciprocating motion vertically, and the broth and the extraction solvent are respectively supplied to the upper and lower portions of the column; and (c) reacting the extract with an alcohol having 4 or less carbons or a mixture thereof using an esterification reactor, thus obtaining alkyl butyrate.

The technical problem of the present invention is not limited to the foregoing, and the other technical problems will be understood clearly to those skilled in the art from the following description.

Technical Solution

According to an aspect of the present invention, a method of preparing alkyl butyrate is provided, which includes (a) producing a broth including a butyrate salt via fermentation using a butyric acid production strain; (b) adding an inorganic acid other than carbonic acid, or carbon dioxide to the broth so that the butyrate salt is converted into butyric acid, and then extracting butyric acid with an extraction solvent by means of a continuous extraction apparatus, thus obtaining an extract containing butyric acid, wherein the continuous extraction apparatus is configured such that an extraction column is provided with a plurality of plates which perform a reciprocating motion vertically, and the broth and the extraction solvent are respectively supplied to the upper and lower portions of the column; and (c) reacting the extract with an alcohol having 4 or less carbons or a mixture thereof using an esterification reactor, thus obtaining alkyl butyrate.

Advantageous Effects

According to the present invention, alkyl butyrate can be prepared with price competitiveness while minimizing the consumption of energy because of efficient extraction of butyric acid from a broth using microorganisms, without the need for additional separation from an extraction solvent.

Also, the thus-produced alkyl butyrate can be directly used as bio-fuel oil, without the need for additional subsequent processes, thus obviating an expensive high-pressure high-temperature catalytic reactor for producing butanol, which is bio-fuel, via hydrolysis of alkyl butyrate.

MODE FOR INVENTION

Hereinafter, a detailed description will be given of the present invention.

According to an aspect of the present invention, a method of preparing alkyl butyrate is provided, which includes (a) producing a broth including a butyrate salt via fermentation using a butyric acid production strain; (b) adding an inorganic acid other than carbonic acid, or carbon dioxide to the broth so that the butyrate salt is converted into butyric acid, and then extracting butyric acid using an extraction solvent by means of a continuous extraction apparatus thus obtaining an extract containing butyric acid, wherein the continuous extraction apparatus is configured such that an extraction column is provided with a plurality of plates which perform a reciprocating motion vertically, and the broth and the extraction solvent are respectively supplied to the upper and lower portions of the column; and (c) reacting the extract with an alcohol having 4 or less carbons or a mixture thereof using an esterification reactor, thus obtaining alkyl butyrate.

Figure 1:
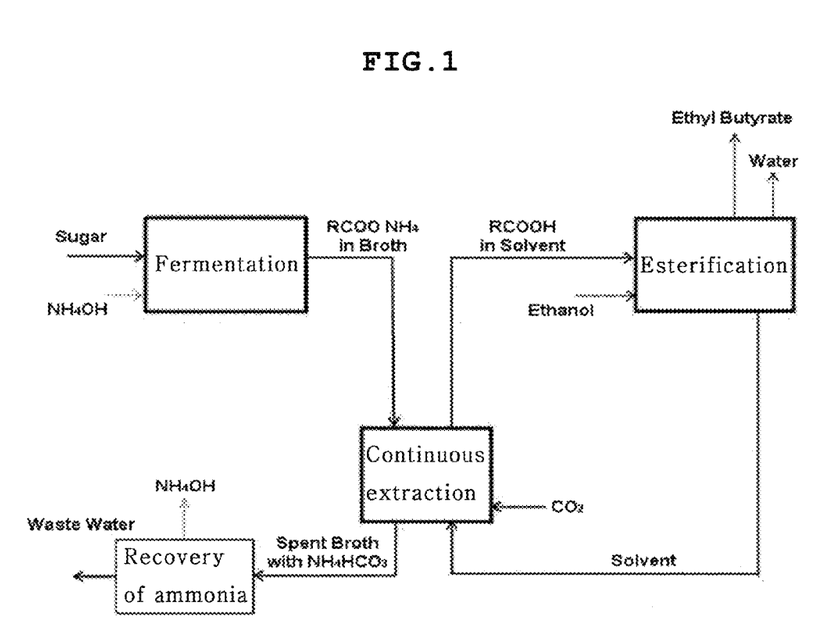
FIG. 1 illustrates a process of preparing ethyl butyrate, by extracting butyric acid using carbon dioxide and an extraction solvent from a fermentation broth including a butyrate salt.
Figure 2:
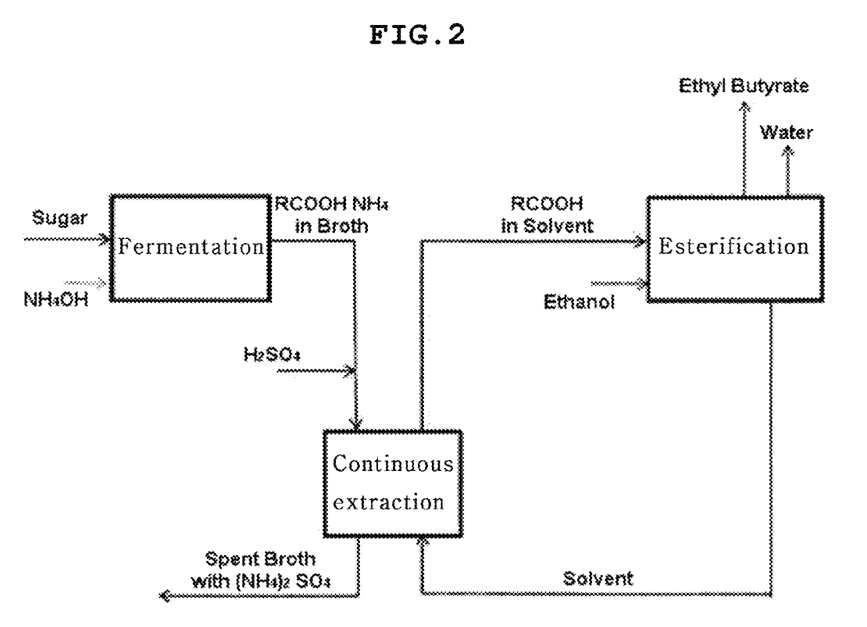
FIG. 2 illustrates a process of preparing ethyl butyrate, by adding sulfuric acid and an extraction solvent to a fermentation broth including a butyrate salt and then extracting butyric acid.

The preparation of alkyl butyrate according to the present invention generally includes, as shown in FIGS. 1 and 2, fermentation, extraction, and esterification.

As illustrated in FIG. 1, a butyrate salt produced via fermentation is converted into butyric acid by means of carbon dioxide in a liquid-liquid extraction column which is a continuous extraction apparatus, and is simultaneously extracted with an extraction solvent. The butyric acid contained in the extraction solvent is converted into ethyl butyrate in the esterification reactor, and is thus discharged as a top product.

As illustrated in FIG. 2, sulfuric acid is added to the broth, so that the butyrate salt is converted into butyric acid, followed by performing extraction and esterification as seen in FIG. 1, without the addition of carbon dioxide, thus producing ethyl butyrate.

The first step in the preparation of alkyl butyrate according to the present invention is to produce a broth including a butyrate salt via fermentation using a butyric acid production strain.

Examples of carbohydrate used for fermentation of butyric acid in the present invention may include not only hexose or pentose but also monosaccharides obtained by hydrolyzing polysaccharides, and preferably include glucose, sugarcane juice obtained from sugarcane, or molasses. Carbohydrate is not particularly limited, and may further include carbohydrate materials including starchy materials such as cassava, etc., which are typically used depending on predetermined purposes.

Examples of the strain for producing butyric acid via fermentation of an aqueous carbohydrate solution include, but are not limited to, genus *Clostridium*, such as *Clostridium tyrobutyricum*, *Clostridium butyricum*, and *Clostridium acetobutylicum*, and may further include microorganisms typically used depending on predetermined purposes.

In the case where carbohydrate is fermented using the genus *Clostridium*, butyric acid is produced together with biogas including hydrogen and carbon dioxide. The biogas produced in the course of fermentation of butyric acid has a composition of hydrogen and carbon dioxide at a volume ratio of about 1:1.

Butyric acid in the broth produced from the butyric acid production strain is provided in the form of a butyrate salt coupled with a monovalent or divalent cation, rather than the form of a free acid. This is because the activity of microorganisms may be lowered when pH of the broth decreases due to accumulation of butyric acid in the broth, and thus a basic material is typically added to uniformly maintain pH of the broth. Accordingly, butyric acid of the broth is provided in the form of a butyrate salt coupled with a cation, for example, ammonium butyrate or calcium butyrate coupled with a monovalent or divalent cation, but is not limited thereto, and may further include any inorganic material typically used to adjust pH depending on predetermined purposes. The pH of the broth may be 4 to 6.5, and preferably 5.5 to 6.5.

Figure 3:
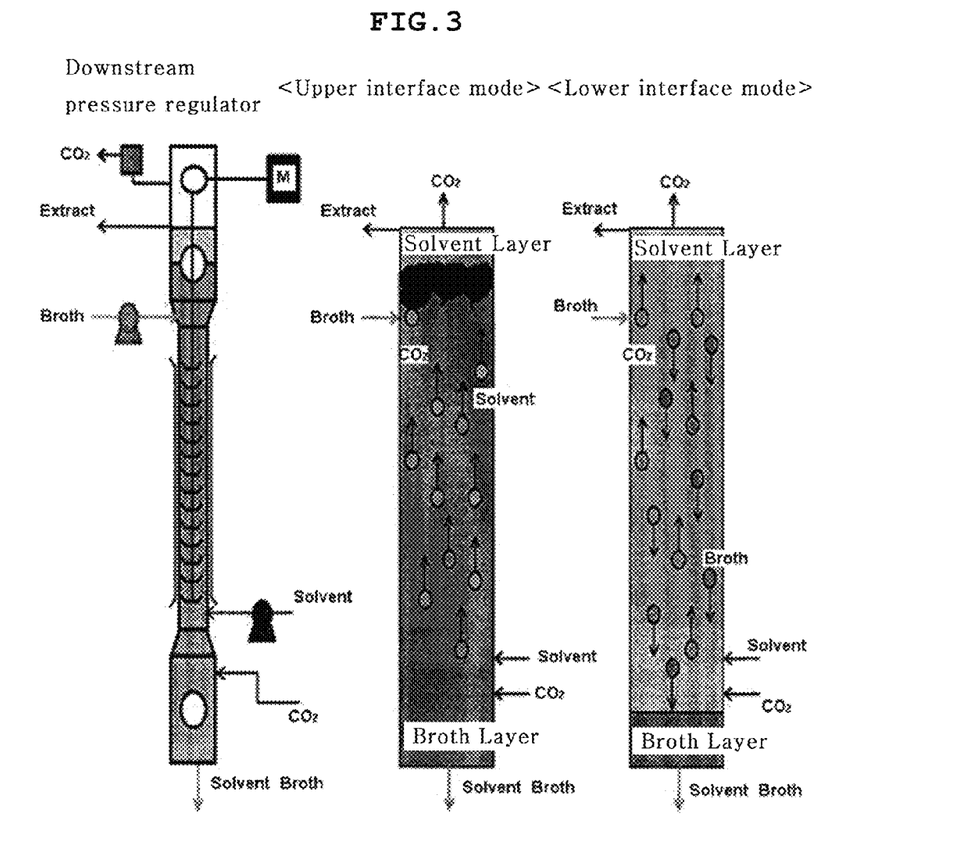
FIG. 3 illustrates a carbon dioxide pressure type continuous extraction apparatus for extracting butyric acid using an extraction solvent from a fermentation broth including a butyrate salt, and the upper interface mode and the lower interface mode of the extraction apparatus.

After production of the broth, the broth is added with an inorganic acid other than carbonic acid, or carbon dioxide, so that the butyrate salt is converted into butyric acid, which is then extracted with an extraction solvent using a continuous extraction apparatus, thus obtaining an extract containing butyric acid. As illustrated in FIG. 3, the continuous extraction apparatus is configured such that an extraction column is installed with a plurality of plates (e.g., perforated plates tied to the rode) which perform a reciprocating motion vertically, therein and the broth and the extraction solvent are respectively supplied to the upper and lower portions of the column.

The extraction column of the continuous extraction apparatus is not packed with a packing material, and has plates which perform a reciprocating motion vertically by means of a motor, so that the broth droplets moving downwards are uniformly dispersed in the extraction solvent flowing upwards, or the extraction solvent droplets moving upwards are uniformly dispersed in the broth flowing downwards, thus increasing contact efficiency of the broth and the extraction solvent and avoiding formation of an emulsion between the broth and the extraction solvent.

In the case where sulfuric acid as the inorganic acid other than carbonic acid is added to the broth, a conversion into butyric acid is comparatively high. However, the ammonium salt such as ammonium butyrate present in the broth produces ammonium sulfate, making it difficult to recover ammonia from the ammonium salt of the broth to reuse it.

Upon extraction, in the case where carbon dioxide is used, carbon dioxide should be supplied at high pressure to increase a conversion into butyric acid. Unlike use of sulfuric acid, however, the ammonium salt such as ammonium butyrate present in the broth produces ammonium bicarbonate, and thus ammonia or aqueous ammonia may be recovered from the ammonium salt and thus reused in the production of the broth. According to an embodiment of the invention, ammonium bicarbonate contained in a spent broth is decomposed into aqueous ammonia and carbon dioxide at 60° C. or higher. When the temperature of the spent broth is further increased to 100° C., ammonia may be evaporated from the spent broth, and then condensed and thus recovered.

As such, the reaction for converting ammonium butyrate into butyric acid by means of carbonic acid is a reversible reaction as represented below, and thus an inverse reaction may also occur, wherein ammonium bicarbonate is coupled with butyric acid and thus converted into ammonium butyrate. Such an inverse reaction is suppressed in proportion to an increase in pressure of carbon dioxide and an increase in distribution coefficient of an extraction solvent with respect to butyric acid. Also, the inverse reaction may be suppressed so long as the produced ammonium bicarbonate may be removed, thus increasing extraction efficiency.

In the present invention, the case where an interface between the broth layer and the extraction solvent layer is maintained so as to exceed the middle position of the column is called the upper interface mode, and the case where such an interface is maintained below the middle position of the column is called the lower interface mode.

In an embodiment of the invention, when an inorganic acid other than carbonic acid is used, butyric acid may be extracted regardless of the interface mode depending on the interface between the broth layer and the solvent layer in the continuous extraction apparatus, but the extraction efficiency of the upper interface mode is higher than that of the lower interface mode.

In an embodiment of the invention, when carbon dioxide is used upon extraction of the broth, the interface between the extraction solvent layer and the broth layer is preferably maintained in the lower interface mode, that is, at the position below the middle position of the column. More preferably, carbon dioxide is supplied to the lower portion (or end) of the solvent layer in the continuous extraction apparatus, and the interface between the extraction solvent layer and the broth layer is located below the position at which carbon dioxide is supplied.

In the case where extraction is carried out in the lower interface mode using carbon dioxide, three phases including a broth phase, an extraction solvent phase and an undissolved carbon dioxide bubble phase are present, thus efficiently extracting butyric acid.

In an embodiment of the invention, the vertical vibration frequency of the plates in the extraction column of the continuous extraction apparatus may be 100 or more cycles/min, and the discharge pressure of carbon dioxide may be 10 bar or more. If the discharge pressure of carbon dioxide is less than 10 bar, it is difficult to extract 90% or more of butyric acid even in the presence of the mixture solvent including alkylamine having good extraction efficiency.

In an embodiment of the invention, the amount of added carbon dioxide should be larger than the amount capable of being dissolved in the solvent and the broth, so that desired inner pressure of the column may be maintained while the undissolved bubble phase is present. As the amount of undissolved carbon dioxide increases, extraction efficiency may be improved, but when the amount thereof is excessively increased, an emulsion phenomenon is observed.

The extraction solvent is not particularly limited, but may include isooctanol, alkylamine, or a mixture thereof. In an embodiment of the invention, in the case where extraction is performed using carbon dioxide, the use of a solvent including alkylamine is particularly desirable.

After production of the extract in the present invention, the extract is reacted with an alcohol having 4 or less carbons, alkyl butyrate or a mixture thereof using an esterification reactor, and is thus converted into alkyl butyrate.

Upon conversion into alkyl butyrate, an acid catalyst is used, and a strong acidic ion exchange resin is particularly useful.

If the extraction solvent includes alkylamine in the previous step, the esterification is carried out using a distillation type esterification reactor, instead of a typical reactor.

When the butyric acid extract contains alkylamine, an acid catalyst such as a strong acidic ion exchange resin may be strongly coupled with alkylamine, undesirably losing the activity of the catalyst. Hence, a typical esterification reactor cannot be used. In an embodiment of the invention, when a distillation type esterification reactor as illustrated in FIG. 4 is used, butyric acid may be reacted with ethanol to prepare ethyl butyrate, while preventing the reaction between alkylamine of the extract and the acid catalyst.

Figure 4:
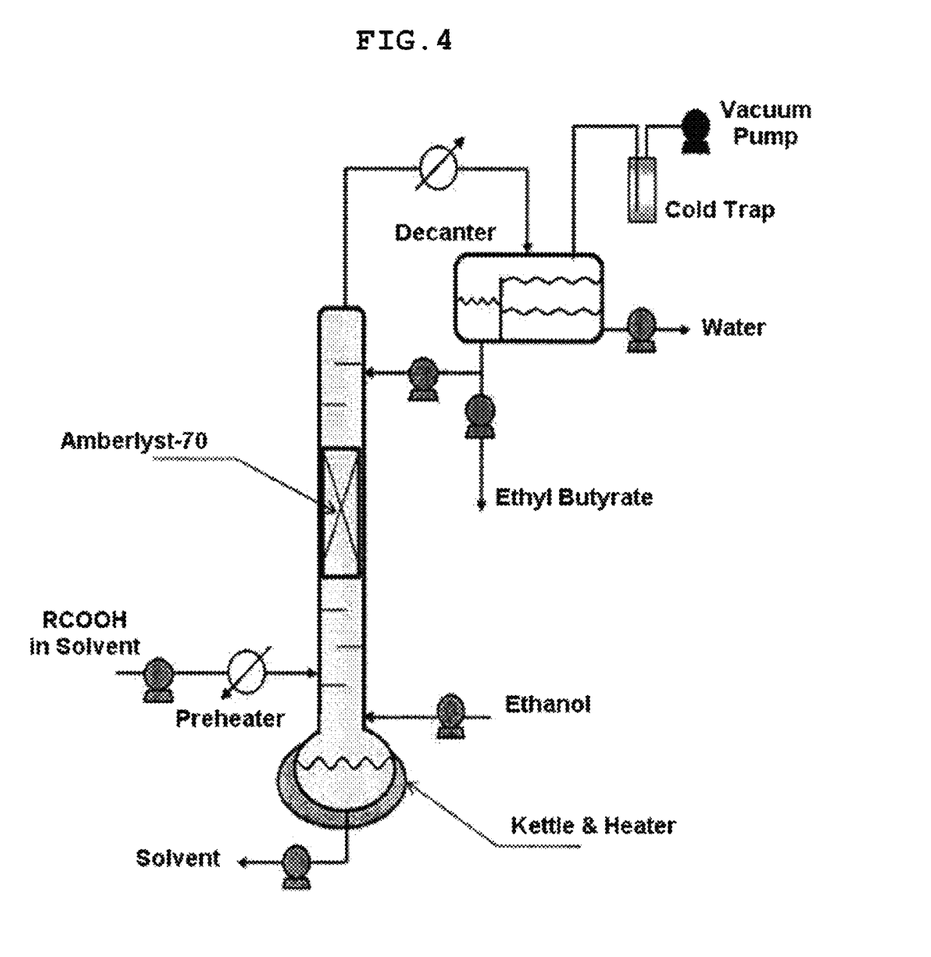
FIG. 4 illustrates a distillation type esterification reactor for preparing ethyl butyrate by reacting butyric acid of the extract with ethanol.

As illustrated in FIG. 4, the extract containing butyric acid having a boiling point of 163° C. is supplied to the lower portion (or end) of the distillation column together with ethanol having a boiling point of 79° C. While the esterification takes place in the course of passing the vapor thereof through the column packed with a strong ion exchange resin, ethyl butyrate having a boiling point of 121° C. and water having a boiling point of 100° C. are produced, discharged from the upper portion of the column, and then condensed, so that phase separation between an ethyl butyrate layer and a water layer occurs using a decanter. As such, part of the ethyl butyrate layer is recirculated to the upper portion of the column so that the temperature of the upper portion of the column is controlled, and thus unreacted butyric acid having a comparatively high boiling point is not moved well to the upper portion of the column, whereby the inside of the column is maintained in a state of the concentration of butyric acid being high.

Thus, in the case where the extract supplied to the reactor includes alkylamine, even when part of alkylamine is vaporized and supplied to the lower portion of the column, it may be converted into alkylammonium butyrate which is difficult to vaporize via reaction with butyric acid in the column, discharged from the lower portion of the column, and turned back to a reboiler, and thus does not affect the strong ion exchange resin in the column.

The reboiling temperature of the distillation type reactor should be higher than 130° C. so as to decompose alkylammonium butyrate, but is preferably set to less than 200° C. so that alkylamine is not damaged. Also, in order to suppress side-reactions, the temperature of the strong ion exchange resin in the column should be maintained at 110° C. or less. To satisfy such temperature requirements, the distillation type esterification may be performed under vacuum conditions of 200 to 500 torr.

In an embodiment of the invention, alkyl butyrate is methyl butyrate, ethyl butyrate, propyl butyrate, butyl butyrate or a mixture thereof.

A better understanding of the present invention may be obtained via the following examples which are set forth to illustrate, but are not to be construed as limiting the present invention.

EXAMPLE 1

Fermentation of Butyric Acid

30 L of sugarcane juice (sugar concentration: 120 g/L) was placed into a 50 L anaerobic fermenter, inoculated with *Clostridium tyrobutyricum*, and then maintained at 37° C., and the pH of the broth was kept to 6.0 using aqueous ammonia.

After production of gas from the broth was decreased to be lower than a predetermined level, biomass was separated from the broth using a continuous centrifuge.

As such, the production rate of butyric acid was 0.9-1 g/L-h, and the obtained broth contained butyric acid at a concentration of 50 g/L and acetic acid at a concentration of 6.5 g/L.

EXAMPLE 2

Extraction of Butyric Acid from Broth (Upper Interface Mode)

Sulfuric acid was added to the broth obtained in Example 1 so that the pH of the broth was adjusted to 2.0. As such, the concentration of butyric acid was measured to be 44 g/L.

A continuous extraction apparatus (vertical Karr extraction column) having a diameter of 25.4 mm and a length of 3,000 mm was filled with the broth via the upper inlet. The column was provided with 70 plates having a specific shape and performing a reciprocating motion vertically by a motor so that isooctanol as an extraction solvent was dispersed in the broth to extract butyric acid from the broth. As illustrated in FIG. 3, this column was operated in the upper interface mode in which the interface between the broth layer and the solvent layer was continuously maintained at the upper position of the column.

The broth was supplied at 2,000 g/h to the upper portion of the column, and the extraction solvent was supplied at 1,000 g/h to the lower portion of the column, and carbon dioxide was not added. The vertical vibration frequency of the plates was 60 cycles/min, and the column temperature was maintained at 40° C. The extract containing butyric acid extracted by the extraction solvent was discharged from a position higher than the inlet of the broth, and the butyric acid-removed spent broth (raffinate) was discharged from a position lower than the inlet of the extraction solvent. While the entire operation was carried out in steady state, 99.5% or more of butyric acid of the broth was extracted with the extraction solvent.

COMPARATIVE EXAMPLE 1

Extraction of Butyric Acid from Broth Using Carbonic Acid (Upper Interface Mode)

The broth at pH of 6.0 obtained in Example 1 was used unchanged without additional use of sulfuric acid.

The broth was extracted in the same upper interface mode using the same continuous extraction apparatus as in Example 2, with the exception that carbon dioxide was supplied at 2 L/min to the lower portion (or end) of the column as shown in FIG. 3 and the pressure of the space filled with carbon dioxide above the solvent layer was maintained at 30 bar using a downstream pressure regulating valve.

However, while a severe emulsion was created at the upper portion of the column, the steady-state operation was impossible. Although several attempts were made to perform the process, the steady-state operation could not be conducted.

Undissolved carbon dioxide droplets moving toward the upper portion of the column via the broth layer were mixed with extraction solvent droplets moving toward the lower portion of the column via the broth, thus making an emulsion, and such an emulsion caused problems at the interface between the solvent layer and the broth layer, which was observed with a glass window equipped to the continuous extraction apparatus.

EXAMPLE 3

Extraction of Butyric Acid from Broth Using Carbonic Acid (Lower Interface Mode)

The broth at pH of 6.0 obtained in Example 1 was used unchanged without additional use of sulfuric acid.

The broth was extracted in the lower interface mode using the same continuous extraction apparatus as in Example 2.

The column was packed with isooctanol via the lower inlet, the vertical vibration frequency of the plates thereof was set to 60 cycles/min, the column temperature was 40° C., and carbon dioxide was supplied at 2 L/min to the lower portion (end) of the column and the pressure of the space filled with carbon dioxide above the solvent layer was maintained at 30 bar using a downstream pressure regulating valve. As the pressure of carbon dioxide was not maintained at 30 bar and decreased over time, the supply of carbon dioxide was increased to 5 L/min and thus the pressure thereof was maintained to 30 bar.

The broth was supplied at 2,000 g/h to the upper portion of the column, and the extraction solvent was supplied at 1,000 g/h to the lower portion of the column. As such, no emulsion was created, and a steady-state operation was conducted.

While the vertical vibration frequency of the plates and the supply rate of the extraction solvent were changed, testing was carried out. The results are shown in Table 3 below.

TABLE 3

| Butyric acid extraction efficiency | | Supply rate of Extraction solvent | | |
|---|---|---|---|---|
| | | 1,000 g/L | 2,000 g/L | 3,000 g/L |
| Vertical vibration frequency of plates (cycles/min) | 60 | 42 | — | — |
| | 100 | 56 | — | — |
| | 140 | 60 | 77 | 86 |

As the vibration frequency of the plates was increased to 140 cycles/min, extraction efficiency was increased, but when the vibration frequency thereof was increased to 180 cycles/min, the extraction efficiency was not further increased, and a weak emulsion was rather created, and thus operation was carried out at the vibration frequency decreased to 140 cycles/min. However, as shown in FIG. 3, in the lower interface mode wherein undissolved carbon dioxide droplets pass through only the solvent layer moving downwards, the extent of generation of the emulsion was comparatively weak.

Also, when the supply rate of the extraction solvent was increased, extraction efficiency was increased, but the concentration of butyric acid in the extract was undesirably lower than that of butyric acid in the broth.

The reason why limitations are imposed on increasing the extraction efficiency is considered to be due to an inverse reaction by ammonium bicarbonate contained in the butyric acid-free spent broth.

The pH of the spent broth thus obtained was about 7.0-7.5. When the spent broth was placed in a vacuum evaporator and heated to 80° C. or higher, the pH of the spent broth was increased to 9 or more, and then continuous heating resulted in pH decreasing to 5.8-6.2 . From this, it can be indirectly seen that ammonium bicarbonate in the spent broth was decomposed into ammonia, carbon dioxide and water, and then ammonia was evaporated off from the broth. On the other hand, aqueous ammonia was condensed and recovered to a receiver flask provided to the vacuum evaporator. The aqueous ammonia thus recovered may be reused in the fermentation of butyric acid.

EXAMPLE 4

Extraction of Butyric Acid from Broth Using Carbonic Acid (Lower Interface Mode, Using Amine-Mixed Solvent)

The broth at pH of 6.0 obtained in Example 1 was used unchanged without additional use of sulfuric acid, and extraction was carried out in the lower interface mode using the same continuous extraction apparatus as in Example 2.

A solvent mixture of isooctanol and tributylamine at a weight ratio of 8:2 was placed in the column via the lower inlet, and the vertical vibration frequency of the plates of the column was set to 60 cycles/min, the column temperature was 40° C., and carbon dioxide was supplied at 5 L/min to the lower portion (end) of the column and the pressure of the space filled with carbon dioxide above the solvent layer was maintained at 30 bar.

The broth was supplied at 2,000 g/h to the upper portion of the column, and the extraction solvent was supplied at 1,000 g/h to the lower portion of the column, so that no emulsion was created, and the steady-state operation was carried out.

While the vertical vibration frequency of the plates and the pressure of carbon dioxide were changed, testing was carried out. The results are shown in Table 4 below.

TABLE 4

| Butyric acid extraction efficiency | | Carbon dioxide pressure | | |
|---|---|---|---|---|
| | | 30 bar | 20 bar | 10 bar |
| Vertical vibration frequency of plates (cycles/min) | 60 | 88 | — | — |
| | 100 | 96 | — | — |
| | 140 | 99 | 95 | 90 |

When tributylamine having pKb of 3.5 was partially mixed with the extraction solvent, extraction efficiency of butyric acid was greatly improved.

As the pressure of carbon dioxide was decreased, extraction efficiency was lowered. The discharge pressure of carbon dioxide could not be increased to 30 bar or more because of limitations of pressure durability of the continuous extraction apparatus. However, when the pressure is further increased, it is expected to increase extraction efficiency.

EXAMPLE 5

Distillation Type Esterification for Producing Ethyl Butyrate (1)

The extract obtained in Example 2 was used as a feedstock, and the concentration of butyric acid was 13.5% (wt/wt).

In a distillation type esterification reactor as illustrated in FIG. 4, the middle portion of the distillation column was packed with Amberlyst-70Wet which is a strong acidic ion exchange resin available from Rohm & Haas, and the top product was separated into a water layer and an ethyl butyrate layer using a decanter, after which the water layer was discharged off, and the ethyl butyrate layer was discharged as a product. As such, part of ethyl butyrate was recirculated to the top of the column to control the temperature of the top of the column.

The extract was heated to 110° C. using a preheater and then supplied at 3,000 g/hr to the lower portion of the distillation column, whereas ethanol was supplied at 250 g/hr to the upper portion of a kettle without being preheated. As such, the pressure of the top of the column was 300 torr, and the inner temperature of the kettle was 140-145° C.

The entire operation was carried out in steady state, after which a top product comprising 91% of ethyl butyrate and 0.1% of butyric acid was obtained. A bottom product was composed of 92% of octanol and 8% of isooctyl butyrate.

EXAMPLE 6

Distillation Type Esterification for Producing Ethyl Butyrate (2)

The extract obtained in Example 4 was used as a feedstock, and the concentration of butyric acid was 9% (wt/wt) and the concentration of tributylamine was 17.5%.

The same apparatus and operation mode as in Example 5 were used.

The extract was heated to 120° C. using a preheater and then supplied at 3,000 g/hr to the lower portion of the distillation column, whereas ethanol was supplied at 200 g/hr to the upper portion of a kettle without being preheated. As such, the pressure of the top of the column was 300 torr, and the inner temperature of the kettle was 145-150° C.

The entire operation was carried out in steady state, after which a top product comprising 85% of ethyl butyrate and 0.5% of butyric acid was obtained.

When the extract including a basic material such as tributylamine is passed through a typical reactor packed with a strong acidic ion exchange resin such as Amberlyst-70Wet, problems of damage to acidic sites of the catalyst may occur.

However, such damage does not occur when using the distillation type esterification reactor according to the present invention. At the high temperature of the kettle, tributylammonium butyrate is decomposed into butyric acid and tributylamine, and butyric acid is vaporized and thus transferred upwards. As such, a small amount of tributylamine is vaporized and moved upwards together with the butyric acid. However, in the course of passing tributylamine through the column packed with butyric acid at 100° C. or less, tributylamine may react with butyric acid before reaching the catalytic bed packed with a strong acidic ion exchange resin and thus is converted into tributylammonium butyrate which is difficult to exist as a gaseous phase, which is then dropped into the kettle. Hence, this tributylamine is found to have no influence on the catalytic bed.

EXAMPLE 7

Distillation Type Esterification for Producing Butyl Butyrate

The extract obtained in Example 2 was used as a feedstock, and the concentration of butyric acid was 13.5% (wt/wt).

The same apparatus and operation mode as in Example 5 were used.

The extract was heated to 120° C. using a preheater and then supplied at 3,000 g/hr to the lower portion of the distillation column, whereas butanol was heated to 100° C. and then supplied at 400 g/hr to the upper portion of a kettle. As such, the pressure of the top of the column was 200 torr, and the inner temperature of the kettle was 140-145° C.

The entire operation was carried out in steady state, after which a top product comprising 79% of butyl butyrate, 5.5% of butyric acid and 14% of butanol was obtained, which is regarded as an appropriate feedstock for use in hydrogenolysis for producing butanol.

When butyl butyrate is hydrogenolyzed, butanol and unreacted butyl butyrate are obtained as products and other esters are not additionally produced, and thus butanol may be easily separated and purified. On the other hand, when ethyl butyrate is hydrogenolyzed, butyl acetate and butyl butyrate may be partially produced, in addition to butanol and unreacted ethyl butyrate.

The invention claimed is:

1. A method of preparing alkyl butyrate, comprising:
    (a) producing a broth including a butyrate salt via fermentation using a butyric acid production strain;
    (b) converting the butyrate salt in the broth into butyric acid by supply of carbon dioxide and simultaneously extracting butyric acid from the broth using an extraction solvent in a continuous extraction apparatus, to obtain an extract containing butyric acid, wherein the continuous extraction apparatus is configured such that an extraction column is provided with a plurality of plates which perform a reciprocating motion vertically, and the broth and the extraction solvent are respectively supplied to upper and lower portions of the extraction column; and
    (c) reacting the extract with an alcohol having 4 or less carbons or a mixture thereof using an esterification reactor to obtain alkyl butyrate,
    wherein an interface between a broth layer and an extraction solvent layer in the extraction column is maintained below the middle position of the extraction column, and wherein in step (b), carbon dioxide is supplied to a lower portion of the extraction solvent layer in the extraction column, and the interface between the extraction solvent layer and the broth layer is below a position at which carbon dioxide is supplied.

2. The method of claim 1, wherein, when the butyrate salt is ammonium butyrate in step (a), ammonium bicarbonate is generated in the broth during step (b), and the method further comprises recovering ammonia or aqueous ammonia from a spent broth obtained after step (b) and reusing the recovered ammonia or aqueous ammonia in step (a).

3. The method of claim 1, wherein, when the extraction solvent includes alkylamine, the esterification reactor used in step (c) is a distillation type esterification reactor.

4. The method of claim 1, wherein the alkyl butyrate is methyl butyrate, ethyl butyrate, propyl butyrate, butyl butyrate and mixtures thereof.

5. The method of claim 1, wherein a vertical vibration frequency of the plates of the continuous extraction apparatus is 100 or more cycles/min.

6. The method of claim 1, wherein a discharge pressure of carbon dioxide in the continuous extraction apparatus is 10 bar or more.

* * * * *